United States Patent
Kana et al.

(10) Patent No.: US 10,232,096 B2
(45) Date of Patent: Mar. 19, 2019

(54) TISSUE COLLECTION AND DIVERTIBLE SUCTION VALVE

(71) Applicant: SpineSmith Partners, L.P., Austin, TX (US)

(72) Inventors: Richard J. Kana, Lexington, TX (US); Richard A. Hynes, Melbourne, FL (US)

( * ) Notice: Subject to any disclaimer, the term of this patent is extended or adjusted under 35 U.S.C. 154(b) by 184 days.

(21) Appl. No.: 15/147,603

(22) Filed: May 5, 2016

(65) Prior Publication Data
US 2017/0348468 A1    Dec. 7, 2017

(51) Int. Cl.
*A61M 1/00* (2006.01)
*A61M 39/22* (2006.01)

(52) U.S. Cl.
CPC ........ *A61M 1/0056* (2013.01); *A61M 1/0035* (2014.02); *A61M 39/22* (2013.01)

(58) Field of Classification Search
CPC .............. A61M 1/0056; A61M 1/0035; A61M 1/0007; A61B 2018/00565; F16K 1/20; F16K 5/04; F16K 5/0442
See application file for complete search history.

(56) References Cited

U.S. PATENT DOCUMENTS

| | | | | |
|---|---|---|---|---|
| 3,870,042 A | * | 3/1975 | Viguier | A61M 1/02 604/406 |
| 6,592,769 B1 | * | 7/2003 | Erickson | A61C 17/046 210/521 |
| 6,626,884 B1 | * | 9/2003 | Dillon | A61M 1/02 600/573 |

* cited by examiner

*Primary Examiner* — Tatyana Zalukaeva
*Assistant Examiner* — Gabriella Burnette
(74) *Attorney, Agent, or Firm* — Winstead PC

(57) ABSTRACT

A device for selectively filtering a substance suctioned from a surgical site includes a valve that may be positioned in a bypass mode and a filtration mode. The valve is placed within a body that includes an inlet and an outlet. In the bypass mode, a first inlet of the valve is adapted to be aligned with the body inlet. The first inlet guides the substance through a bypass passageway to the body outlet. In the bypass mode, a bowl and a filter of the body are sectioned off from a flow path of the filtration device such that the bowl and the filter can be removed without interrupting an application of suction to a surgical site by the filtration device. In a filtration mode, a second inlet of the valve is adapted to be aligned with the body inlet to direct the substance into the filter.

16 Claims, 5 Drawing Sheets

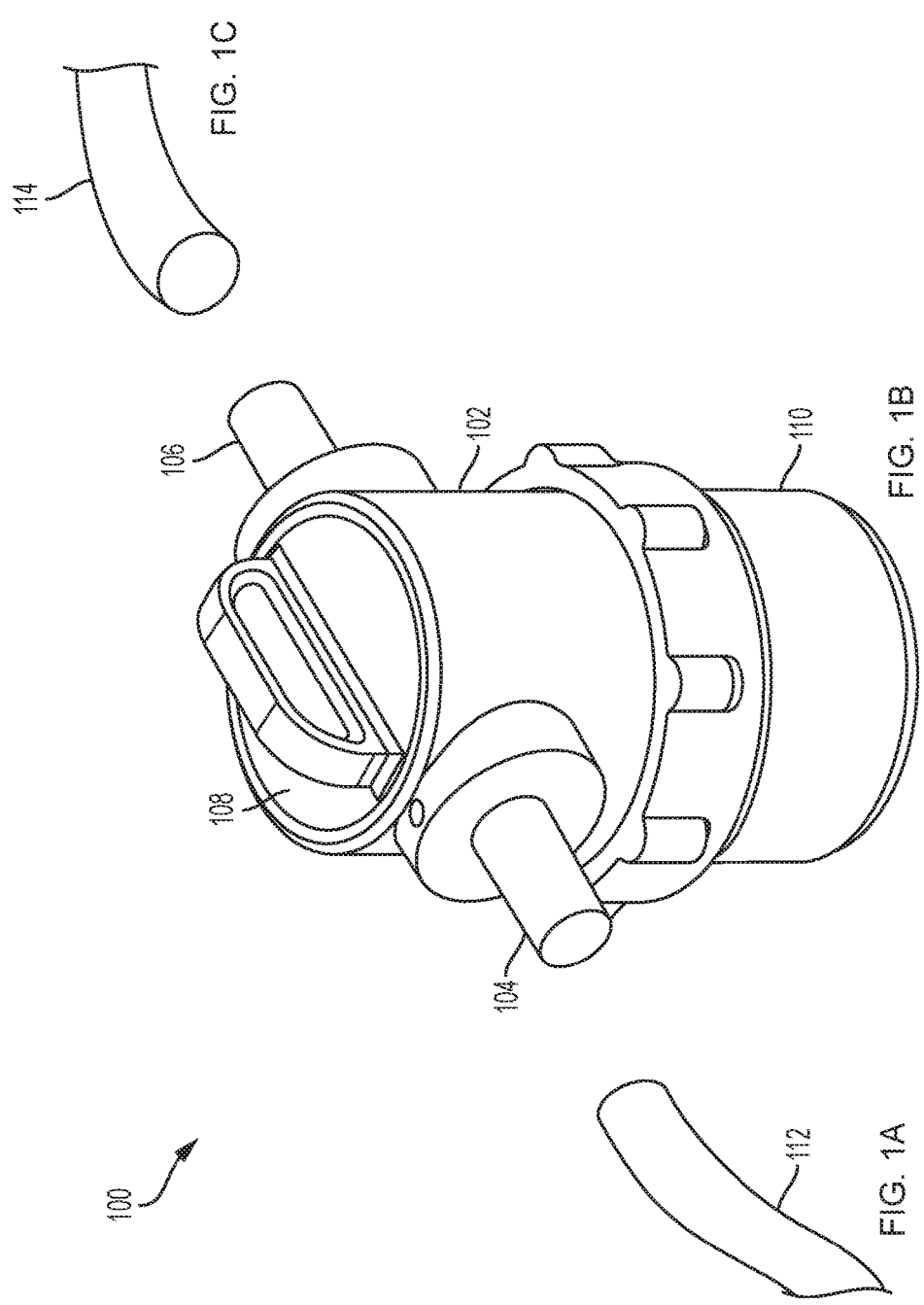

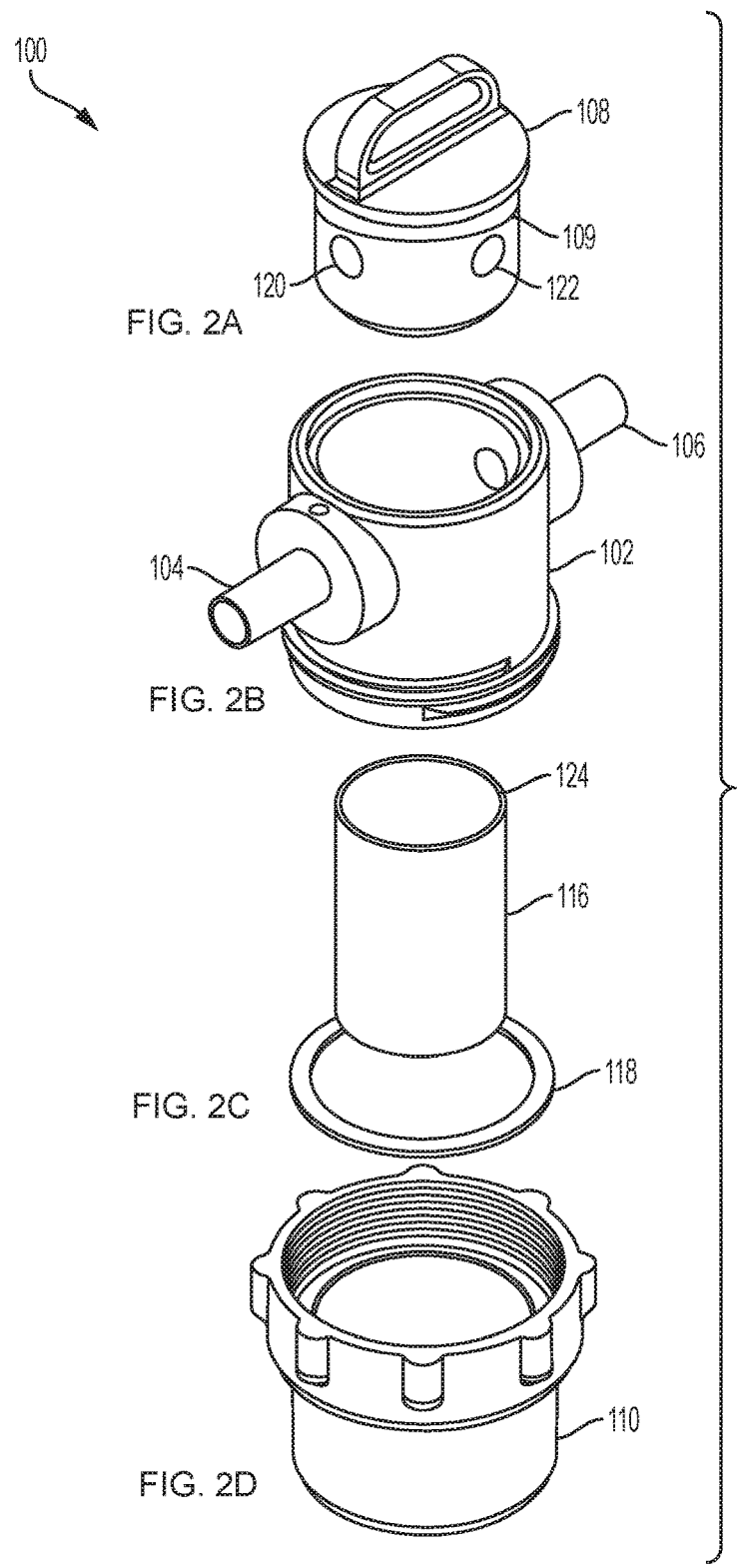

TISSUE COLLECTION AND DIVERTIBLE SUCTION VALVE

TECHNICAL FIELD OF THE INVENTION

The present disclosure relates generally to the field of medicine. More particularly, it concerns a device for applying suction to a surgical site while selectively filtering substances collected from the surgical site.

BACKGROUND OF THE INVENTION

This summary is provided to introduce a selection of concepts that are further described below in the detailed description. This summary is not intended to identify key or essential features of the claimed subject matter, nor is it intended to be used as an aid in limiting the scope of claimed subject matter.

Orthopedic or other surgical procedures often generate various substances and particulates that may be harvested and used. For example, harvested bone may be implemented back into a patient from which it was derived as an autogenous graft material. Harvesting of bone and tissues may be performed in a variety of ways. For example, collection systems are known which include a collection filter located in a suction line of the system. In such systems, having the filter in the path of the only suction line is a problem because suction is not available when the collection filter is removed from the system, which prevents the surgeon from continuing to perform any suction at the surgical site, and may delay the surgery. Furthermore, there may be situations during a surgical procedure that a surgeon desires to provide suction to a surgical site but does not want to filter the suctioned substances. Thus, there is a need for a filtering system that maintains suction even when a filter or bowl has been removed from the system and that can selectively filter suctioned substances.

SUMMARY OF THE INVENTION

During surgery, space around a patient is very limited. Bulky devices and excessive tubing interfere with a user's ability to access the patient. The device of the instant application provides a compact device that is adapted to use a single tube to provide suction to a surgical site.

In a typical embodiment, the device of the instant application allows a user to selectively switch between a material capture mode and a material rejection mode without having to remove a bone capture filter from the suction line or from the housing assembly.

In a typical embodiment, the device of the instant application includes a bowl that can be removed without interrupting suction at a surgical site. The device further permits a user to discriminate between desirable and undesirable substances with the use of a valve. Substances can be collected or diverted according to the preference of the user.

In a typical embodiment, the device of the instant application allows a user to apply suction to a surgical site regardless of whether or not a collection bowl is attached.

In a typical embodiment, the device of the instant application allows harvesting of desirable tissues at the discretion of a user and, since the inventive device can be placed on the sterile field, there is a greatly reduced risk of contamination of the desirable tissues.

In various embodiments, the device of the instant application allows a user to select a bowl and filter of various sizes for larger or smaller collections as desired. Also, the filter screen itself may be interchangeable, presenting either larger openings or finer openings, depending on what form or texture of tissue the user wishes to collect.

Throughout this application, the term "about" is used to indicate that a value includes values that approximate the value described. The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A, 1B and 1C represent an isometric view of a filtration device;

FIGS. 2A, 2B, 2C and 2D represent an exploded assembly view of the filtration device of FIG. 1;

DETAILED DESCRIPTION

Figure 3A:
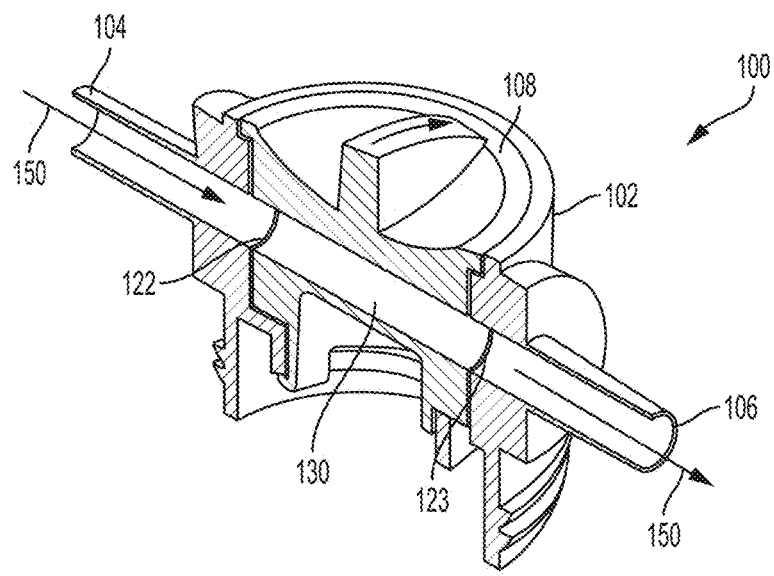
FIG. 3A is a sectioned view of a filtration device in a bypass mode.

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

During a surgical process, various fluids and solids may be suctioned out from a surgical site. Some of the tissues removed during this process are not desirable and are discarded as bio waste product. A problem with typical suction devices is that the suction is always directed through a filter of a suction device. As a result, there is no ability to maintain suction when the filter is removed. For example, during a surgical procedure, the filter may become full or clogged. In order to continue the application of suction to the surgical site, the filter must be removed and replaced. While the filter is being removed, suction can no longer be applied to the patient.

The inventive device allows a user to apply suction to a surgical site, regardless of whether or not a filter and/or collection bowl are attached to the device. Furthermore, the user can selective decide when suctioned substances are filtered. This functionality is possible through the use of a valve that is built into a filtration unit so that the user can select when suctioned substances are routed through the filter unit. In a typical embodiment, valve of the filtration device allows a user to select between a bypass mode and a filtration mode. This arrangement allows the user to discriminate as to which substances are captured during the cleaning and suction of the surgical site. Thus, the inventive device allows the user to easily select which suctioned materials bypass the filter and which materials are collected by the filter for later use. An added benefit of the inventive device is that less unwanted material will be collected during the procedure, thereby reducing the chance for clogging of the screen.

The design and features of the inventive device represent improvements over previous concepts due to its unitary construction (all-in-one), its ability to provide suction when a filter and/or bowl is removed, and its ability to allow a user to be selective in the nature of the materials being filtered.

The device of the instant application is designed to fit within the current and acceptable space requirement frequently encountered in surgical procedures. Because of the way this device operates, it may be placed at any point within a normal suction hose. This allows placement of the device near a surgeon for their own operation of the device, or at a more distant location so that an assistant may engage the filtration or by-pass modes.

Referring now to FIG. 1, an isometric view of a filtration device 100 is shown. The filtration device 100 includes a body 102, a valve 108, and a bowl 110. In a typical embodiment, components of the filtration device 100 may be made from various materials that are capable of being sterilized, such as, for example, various polymers and/or metals. Other materials may be used as desired. The body 102 includes an inlet 104 and an outlet 106 that direct a flow of one or more substances into and out of the device 100. The valve 108 is disposed within the body 102 and is adapted to selectively direct a flow of one or more substances either into a filter or to bypass the filter. In a typical embodiment, the valve 108 may be rotated to select between a bypass mode and a filtration mode (see FIGS. 2A and 2B, respectively). In a typical embodiment, rotation of the valve 108 is done manually by a user. In some embodiments, rotation of the valve 108 may be automated via a motor and the like. In a typical embodiment, the filtration device 100 further includes a removable bowl 110. The bowl 110 assists with the filtering of the one or more substances that enter the filtration device, which will be discussed in more detail below.

The inlet 104 is adapted to be coupled to a hose 112. In a typical embodiment, a first end of the hose 112 is attached to the inlet 104 and a second end of the hose 112 is used for applying suction to, for example, a surgical site. The second end of the hose 112 may be attached to various suction tools commonly used during surgical procedures. The suction tool is used to collect one or more substances, such as, for example, tissues and fluids, from the surgical site. The collected one or more substances are directed through the hose 112 and into the filtration device 100 via the inlet 104. The inlet 104 then directs the one or more substances into the valve 108. When the valve 108 is in bypass mode, the valve 108 directs the one or more substances through the filtration device 100 without first passing through a filter. When the valve 108 is in the filtration mode, the valve 108 directs the one or more substances through a filter disposed within the bowl 110. The one or more substances are divided into a retentate portion that is retained within the filter and a permeate portion that passes through the filter. The permeate portion that passes through the filter is directed out of the filtration device 100 via the outlet 106. In a typical embodiment, the outlet 106 is adapted to be coupled to a hose 114. A first end of the hose 114 is attached to the outlet 106 and a second end of the hose 114 is attached to, for example, a suction pump. The suction pump applies suction through the hose 114 to draw the one or more substances from the surgical site into to the filtration device 100 via the hose 112. The permeate portion then passes through the hose 114 and may be collected or discarded as desired.

Figure 5A:
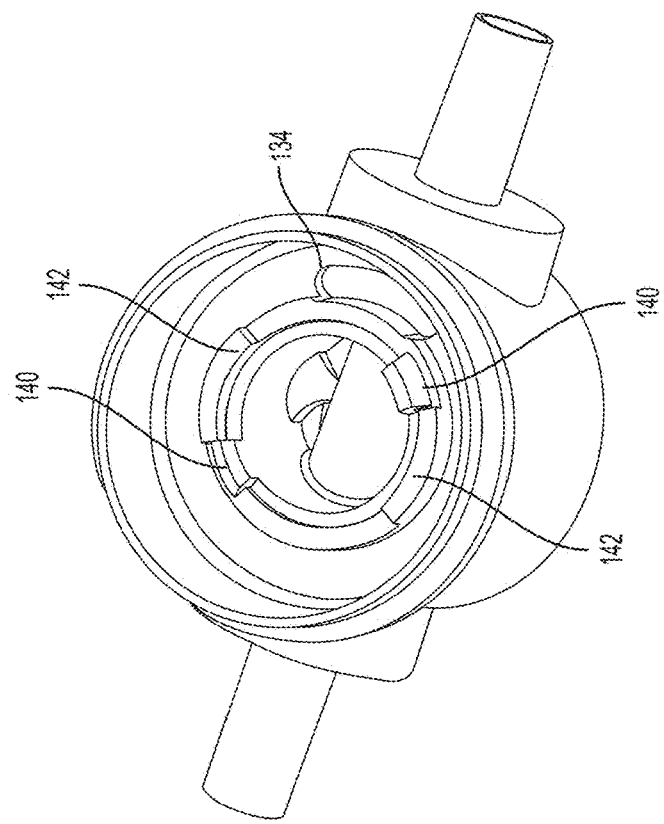
FIG. 5A is a bottom view of a filtration device in a filtration mode.

FIG. 2 is an exploded assembly view of the filtration device 100 of FIG. 1. In a typical embodiment, the valve 108 is rotatably secured to the body 102. The valve 108 is selectively rotatable between two positions to enable the bypass mode and the filtration mode. In the embodiment shown in FIG. 2, the valve 108 includes an o-ring 109 that creates a seal between the valve 108 and the body 102. In other embodiments, the o-ring 109 may not be needed if, for example, mating surfaces of the body 102 and the valve 108 sufficiently seal the device 100. In the filtration mode (as shown in FIGS. 1, 2B, and 5A), a filtration inlet 120 of the valve 108 is aligned with the inlet 104. The valve 108 may be rotated into a second position to align a bypass inlet 122 with the inlet 104. The filtration inlet 120 and the bypass inlet 122 will be discussed in more detail below.

The body 102 is further adapted to receive the filter 116 and the bowl 110. In a typical embodiment, an o-ring 118 is positioned within an opening of the bowl 110 to create a seal between the bowl 110 and the body 102. As shown in FIG. 2, each of the body 102 and the bowl 110 include threads that interlock to secure the bowl 110 to the body 102. In other embodiments, the bowl 110 may be secured to the body 102 with various other connection types, such as, for example, clamps and the like. The filter 116 is adapted to couple to the body 102 to ensure that the one or more substances that enter the inlet 120 are directed into the filter 116. In a typical embodiment, the filter 116 includes open end 124 that slides over a portion of the body 102 to form a sleeve-like coupling. The open end 124 receives the one or more substances that enter the filtration inlet 120. The filter 116 may be selected from a variety of filter types comprising a variety of filter mediums and a variety of pore sizes. In a typical embodiment, the type of filter selected depends upon the type of substances being collected and the size of a component of the substances that is desired to be collected. As the one or more substances enter the filter 116, a retentate portion is collected in the filter 116 and a permeate portion passes through the filter 116 and is collected in the bowl 110. In a typical embodiment, the suction applied to the filtration device 100 causes the permeate portion to be removed from the bowl 110 via the outlet 106. Thus, the one or more substances may be separated into two collectable components: the retentate portion collected in the filter 116 and the permeate portion that can be collected downstream of the filtration device 100.

Referring now to FIG. 3A, a sectioned view of the filtration device 100 with the valve 108 oriented in the bypass mode is shown. Arrows 150 indicate a direction of suction through the filtration device 100. In the bypass mode, the one or more substances enter the inlet 104 and are fed through a bypass passage 130 of the valve 108 and out of the outlet 106. Thus, in the bypass mode, a user can prevent unwanted substances from passing through the filter 116. The ability to select when filtration occurs reduces clogging of the filter 116, which increases an amount of substances that can be removed from a treatment site before the filter 116 needs to be replaced. A substance may be unwanted for various reasons. For example, the substance may be unwanted because a sufficient amount of the material has already been collected, the filter 116 is full or clogged, or the material currently being suctioned is not the material desired for collection. Because the bypass passage 130 completely closes the flow path of the material from the bowl 110, suction is maintained even if the bowl 110 is removed from the filtration device 100. Therefore, in the bypass mode, the bowl 110 and the filter 116 can be removed and replaced as desired without interrupting an ability of the filtration device 100 to provide suction to a surgical site.

Figure 3B:
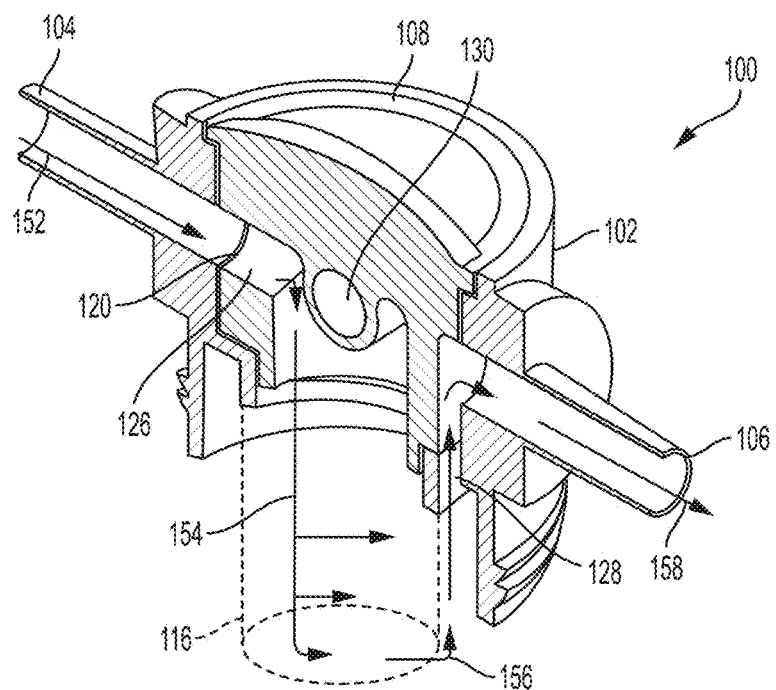
FIG. 3B is a sectioned view of a filtration device in a filtering mode.

Referring now to FIG. 3B, a sectioned view of the filtration device 100 with the valve 108 oriented in the filtration mode is shown. Arrow 152 indicates a direction of flow of the one or more substances into the inlet 104 of the filtration device 100. When the filtration device 100 is in the filtration mode, the inlet 120 is aligned with the inlet 104. The inlet 120 guides the one or more substances into a filtration inlet passage 126. The filtration inlet passage 126 directs the material to the filter 116 (the filter 116 is shown with a dashed outline). Arrows 154 indicate the direction of flow of the one or more substances into the filter 116. Once the one or more substances have entered the filter 116, the one or more substances are separated into a retentate portion that remains trapped within the filter 116 and a permeate portion that passes through the filter 116. Arrows 156 indicate the flow path of the permeate portion that has passed through the filter 116. As shown in FIG. 3B, the permeate portion travels up from the bowl 110 and enters a filtration outlet passage 128. Once the permeate portion has entered the filtration outlet passage 128, it is directed out of the filtration device 100 via the outlet 106.

As shown in FIGS. 3A and 3B, the inlet 104, the inlet 120, the inlet 122, the outlet 106, the outlet 123, and an exit portion of the filtration outlet passage 128 are all coplanar. The coplanar arrangement of these passageways enables the valve 108 to switch between the filtration and bypass modes by rotating the valve 108.

Figure 4B:
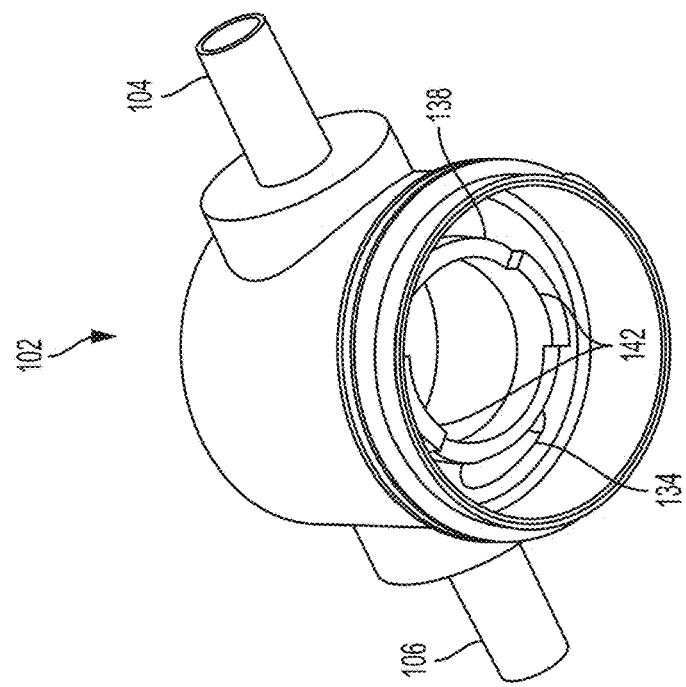
FIG. 4B is a view of a body of a filtration device.
Figure 4A:
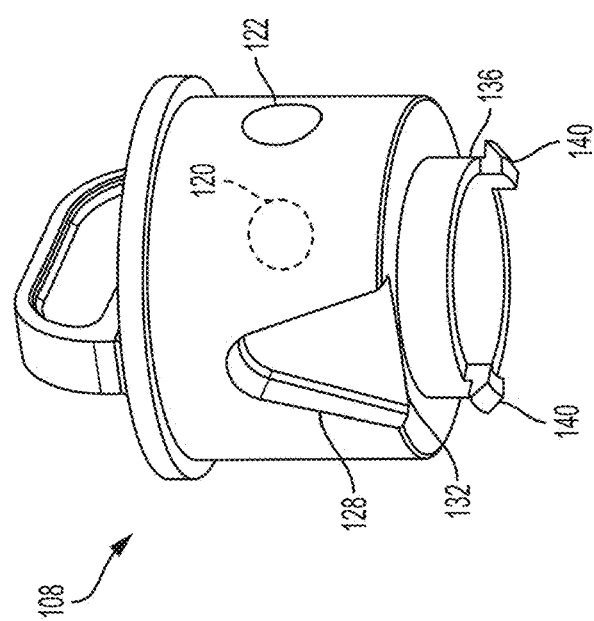
FIG. 4A is a view of a valve of a filtration device.

Referring now to FIGS. 4A and 4B, isometric views of the valve 108 and the body 102, respectively, are shown. FIG. 4A provides a view of the filtration outlet passage 128. In the embodiment shown, the filtration outlet passage 128 includes a wide mouth portion 132 that is adapted to match up with an outlet passage 134 of the body 102 when the filtration device 100 is in the filtration mode. When the filtration device 100 is in the bypass mode, the wide mouth portion 132 is rotated out of alignment with the outlet passage 128. The shape of the wide mouth portion 132 comprises a generally oblong shape. As the permeate portion travels through the filtration outlet passage 128, a cross-section of the outlet passage 128 reduces. The reduction of the cross-section causes a flow rate through filtration outlet passage 128 to decrease. The valve 108 includes a boss 136 that extends downwards from the valve 108. The boss 136 is adapted to fit within a boss 138 of the body 102. As shown in FIG. 4A, the boss 136 includes a pair of stops 140 that extend from a bottom face of the boss 136. In other embodiments, the boss may include one stop or more than two stops as desired. The pair of stops 140 are adapted to both retain the valve 108 within the body 102 and to engage a pair of stops 142 that extend from an end of the boss 138. To install the valve 108 within the body 102, the valve 108 is pressed into the body 102 so that the pair of stops 140 pass through a bore of the boss 138. As the pair of stops 140 pass through the bore of the boss 138, the pair of stops 140 flex inward. Once the pair of stops 140 passes through the bore of the boss 138, they unflex and hook over an edge of the boss 138 to secure the valve 108 to the body 102 with an overlapping fit. The valve 108 may be removed from the body 102 by pinching the pair of stops 140 inwards and pulling the valve 108 away from the body 102. A range of rotation of the valve 108 is determined by the positioning of the pair of stops 142. In a typical embodiment, the range of motion is set to allow the valve 108 to rotate the inlets 120 and 122 into and out of alignment with the inlet 104.

Figure 5B:
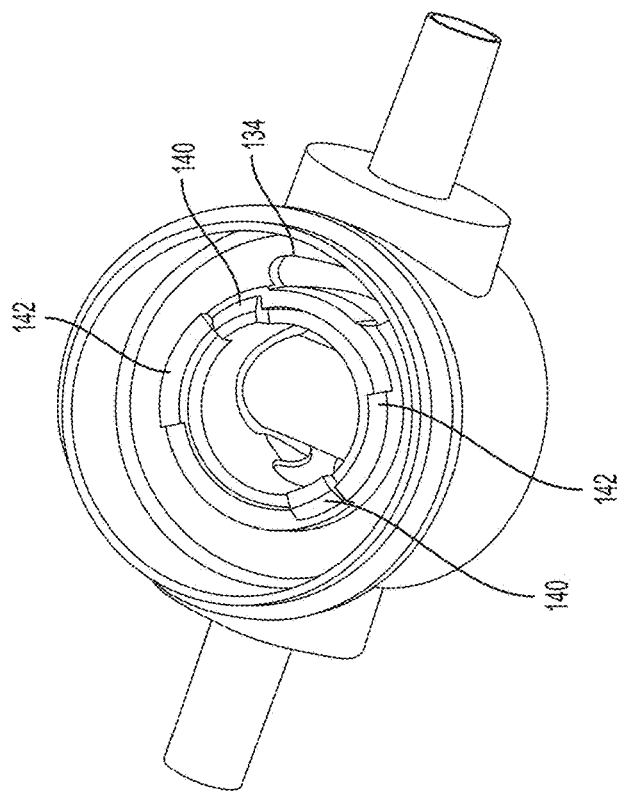
FIG. 5B is a bottom view of a filtration device in a bypass mode.

Referring now to FIGS. 5A and 5B, bottom view of the filtration device 100 in the filtration mode and the bypass mode, respectively, are shown. In the filtration mode, the pair of stops 140 abuts the pair of stops 142 on a first side of the pair of stops 142. In the bypass mode, the pair of stops 140 abuts the pair of stops 142 on a second side of the pair of stops 142. FIGS. 5A and 5B demonstrate how an available amount of rotation of the valve 108 within the body 102 may be controlled. For example, a width of the pair of stops 140 and/or the pair of stops 142 may be altered to change the available amount of rotation.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A filtration device for selectively collecting a substance, the filtration device comprising: a body comprising: a body inlet; and a body outlet; a valve disposed within the body, the valve comprising: a bypass passageway adapted to couple the body inlet to the body outlet when the valve is in a bypass mode; and a filtration inlet passage adapted to couple to the body inlet when the valve is in a filtration mode and a filtration outlet passage adapted to couple to the body outlet when the valve is in a filtration mode; a bowl adapted to couple directly to the body; and a filter adapted to couple directly to the body and adapted to fit within the bowl, wherein an inside of the filter is adapted to receive material from the filtration inlet passage when the valve is in the filtration mode; wherein the valve comprises: a boss that extends toward the bowl; and a flexible stop that extends from the boss and is adapted to couple the valve to the body.

2. The filtration device of claim 1, wherein the body comprises a bore in which the valve is positioned, and wherein the bore of the body further comprises a stop positioned at an end of the bore that interacts with the flexible stop to limit a rotational range of motion of the valve within the body.

3. The filtration device of claim 1, wherein the filtration outlet passage comprises a wide-mouth shape.

4. The filtration device of claim 1, wherein the filtration outlet passage comprises a cross-section that narrows.

5. The filtration device of claim 4, wherein the body comprises an outlet passage with a wide-mouth shape that aligns with the wide-mouth shape of the of the filtration outlet passage.

6. The filtration device of claim 1, wherein the valve comprises an o-ring disposed within a groove formed into a face of a body of the valve.

7. A method of selectively filtering a substance suctioned from a surgical site, the method comprising: placing a suction end of a hose in proximity to a surgical site; applying a suction to the hose to draw a substance into the hose; guiding, with the hose, the substance into a filtration device, the filtration device comprising: a body comprising: a body inlet; and a body outlet; a valve disposed within the body, the valve comprising: a bypass passageway adapted to couple the body inlet to the body outlet when the valve is in a bypass mode; and a filtration inlet passage adapted to couple to the body inlet when the valve is in a filtration mode and a filtration outlet passage adapted to couple to the body outlet when the valve is in a filtration mode; a bowl adapted to couple directly to the body; and a filter adapted to couple directly to the body and adapted to fit within the bowl, wherein an inside of the filter is adapted to receive material from the filtration inlet passage when the valve is in the filtration mode; wherein the valve comprises: a boss that extends toward the bowl; and a flexible stop that extends from the boss and is adapted to couple the valve to the body.

8. The method claim 7, wherein the body comprises a bore in which the valve is positioned, and wherein the bore of the body further comprises a stop positioned at an end of the bore that interacts with the flexible stop to limit a rotational range of motion of the valve within the body.

9. The method claim 7, wherein the filtration outlet passage comprises a wide-mouth shape.

10. The method claim 7, wherein the filtration outlet passage comprises a cross-section that narrows.

11. The method claim 10, wherein the body comprises an outlet passage with a wide-mouth shape that aligns with the wide-mouth shape of the of the filtration outlet passage.

12. The method claim 7, wherein the valve comprises an o-ring disposed within a groove formed into a face of a body of the valve.

13. The method of claim 7, further comprising directing the substance into a filter of the filtration device by orienting the valve in a filtration mode.

14. The method of claim 7, further comprising directing the substance to bypass a filter of the filtration device by orienting the valve in a bypass mode.

15. The method of claim 14, further comprising removing a bowl from the filtration device while continuing to provide suction to the surgical site.

16. The method of claim 14, further comprising replacing the filter of the filtration device while continuing to provide suction to the surgical site.

* * * * *